US00PP18790P3

(12) United States Plant Patent
Snelling et al.

(10) Patent No.: US PP18,790 P3
(45) Date of Patent: May 6, 2008

(54) BLACKCURRANT PLANT NAMED 'BLACKADDER'

(50) Latin Name: *Ribes nigrum*
Varietal Denomination: Blackadder

(75) Inventors: Catherine Snelling, Christchurch (NZ); Geoffrey Langford, Christchurch (NZ)

(73) Assignee: The Horticulture and Food Research Institute of New Zealand Limited, Mr. Albert (NZ)

( * ) Notice: Subject to any disclaimer, the term of this patent is extended or adjusted under 35 U.S.C. 154(b) by 0 days.

(21) Appl. No.: 11/510,270

(22) Filed: Aug. 25, 2006

(65) Prior Publication Data

US 2007/0061928 P1 Mar. 15, 2007

Related U.S. Application Data

(60) Provisional application No. 60/711,902, filed on Aug. 26, 2005.

(51) Int. Cl.
*A01H 5/00* (2006.01)

(52) U.S. Cl. ..... Plt./156

(58) Field of Classification Search ..... Plt./156
See application file for complete search history.

*Primary Examiner*—Kent Bell
*Assistant Examiner*—S. B. McCormick-Ewoldt
(74) *Attorney, Agent, or Firm*—Greenlee Winner and Sullivan PC

(57) ABSTRACT

A new and distinct variety of blackcurrant named 'Blackadder', botanically identified as *Ribes nigrum* is described. The new variety is distinguished from others by its early season bud burst, flowering and harvest. Its bush has an upright habit suitable for machine harvesting. Yields are high and the fruit has high anthocyanin levels and moderate ascorbic acid levels.

6 Drawing Sheets

CROSS-REFERENCE TO RELATED APPLICATION

This application claims the benefit of U.S. provisional application No. 60/711,902 filed Aug. 26, 2005.

Genus and species of plant claimed: *Ribes nigrum.*

Variety denomination: Blackadder.

BACKGROUND TO THE INVENTION

The new variety of blackcurrant, *Ribes nigrum,* was created during the course of a planned plant-breeding program carried out at Lincoln, New Zealand. The new variety was selected from a population of seedlings derived from a controlled cross that was made in 1998, between L20 (unpatented), the seed parent, and L31 (unpatented) the pollen parent. Both parents originated from the breeding program in New Zealand.

Seed from the cross was sown in the field in 1999, in Canterbury, New Zealand. The original plant of the new variety was selected during the 2000–2001 summer.

The new variety was asexually reproduced at Lincoln, New Zealand as hardwood cuttings in winter 2001 and planted into a selection plot for further evaluation. The resulting plants propagated true to type, demonstrating that the characteristics of the new variety are stable and are transmitted without change through succeeding generations.

The new variety is able to be distinguished from its parents on the basis of flowering time. It flowers earlier than both L20 and L31. L20 is resistant to gall mite, the new variety is susceptible. The titratable acidity levels are higher in fruit of the new variety than levels in both L20 and L31. The new variety has also been observed to display less glossy leaves, and less of an upright and vigorous growth habit, compared with the blackcurrant variety Magnus. The new variety flowered earlier and yielded more fruit than Magnus. In comparison with other blackcurrant varieties grown in New Zealand, Bed Ard and Ben Rua, the new variety has been observed to flower earlier than either variety.

SUMMARY OF THE INVENTION

The major characteristics that the new variety exhibits are:

(a) A vigorous, upright growth habit (b) Early bud burst, flowering and maturity, where winter chilling exceeds 1000 hrs below 7° C.

(c) One-year old wood in winter is orange-brown (d) The vegetative buds in winter are slightly held out and are ovate in shape.

(e) Ability to bear black, round fruit of good quality in high yields, well suited to juice.

(f) Susceptible to gall mite.

BRIEF DESCRIPTION OF THE DRAWINGS

The following figures show typical specimens of the new variety in colour as true as is reasonable possible.

DETAILED DESCRIPTION OF THE INVENTION

Figure 1:
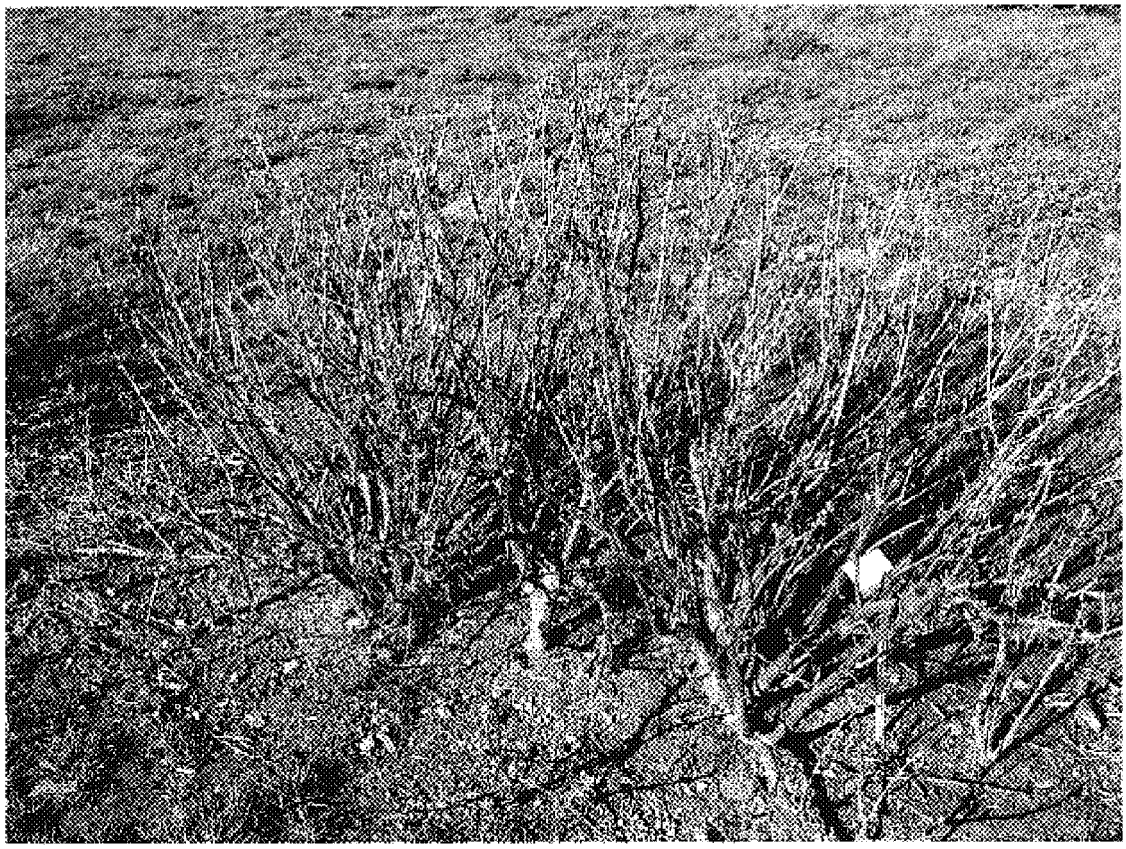
FIG. 1: Upright growth habit of bush, typical of the blackcurrant variety 'Blackadder'.
Figure 2:
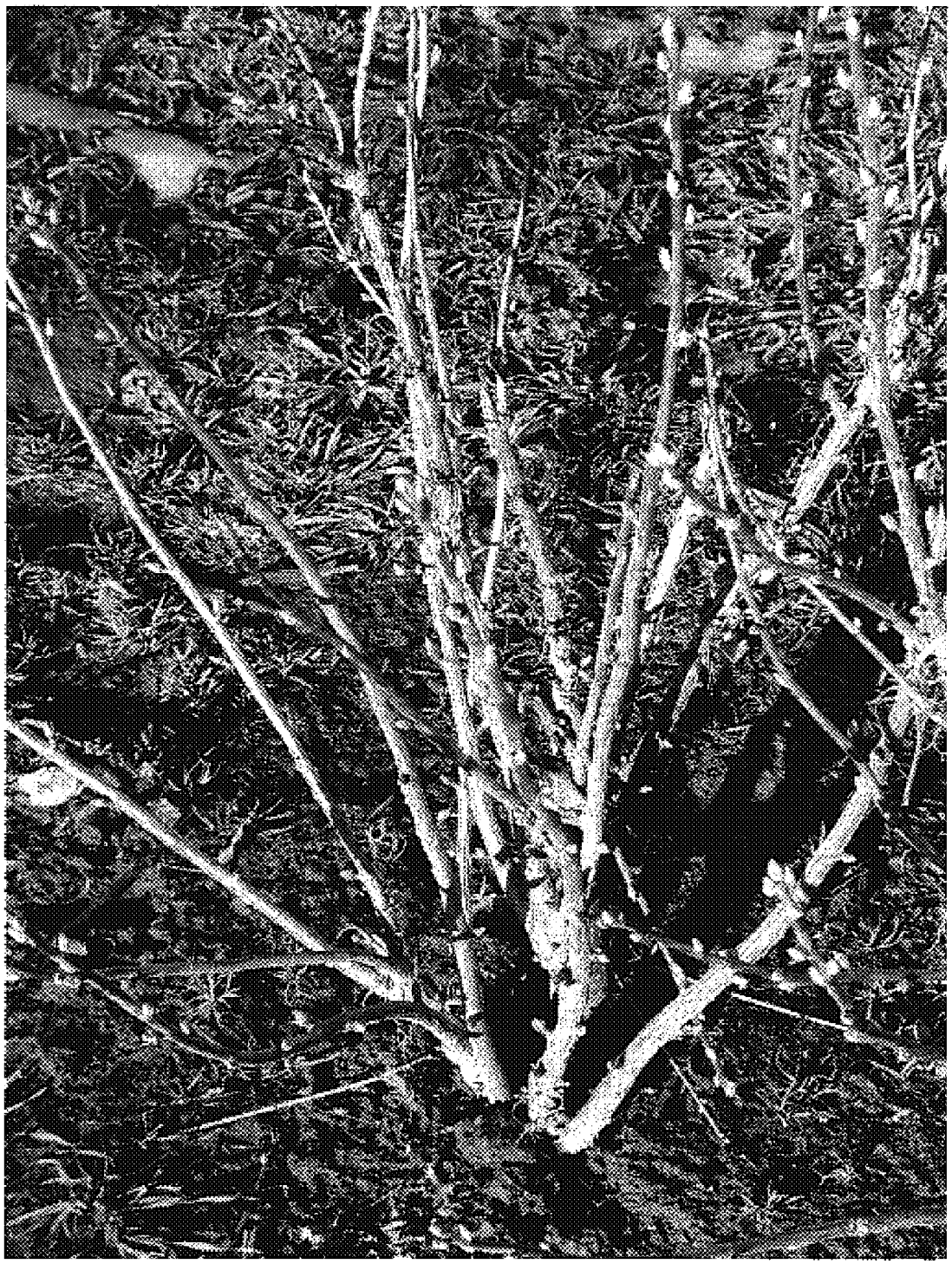
FIG. 2: Colour of wood of one-year old shoots, typical of the blackcurrant variety 'Blackadder'.
Figure 3:
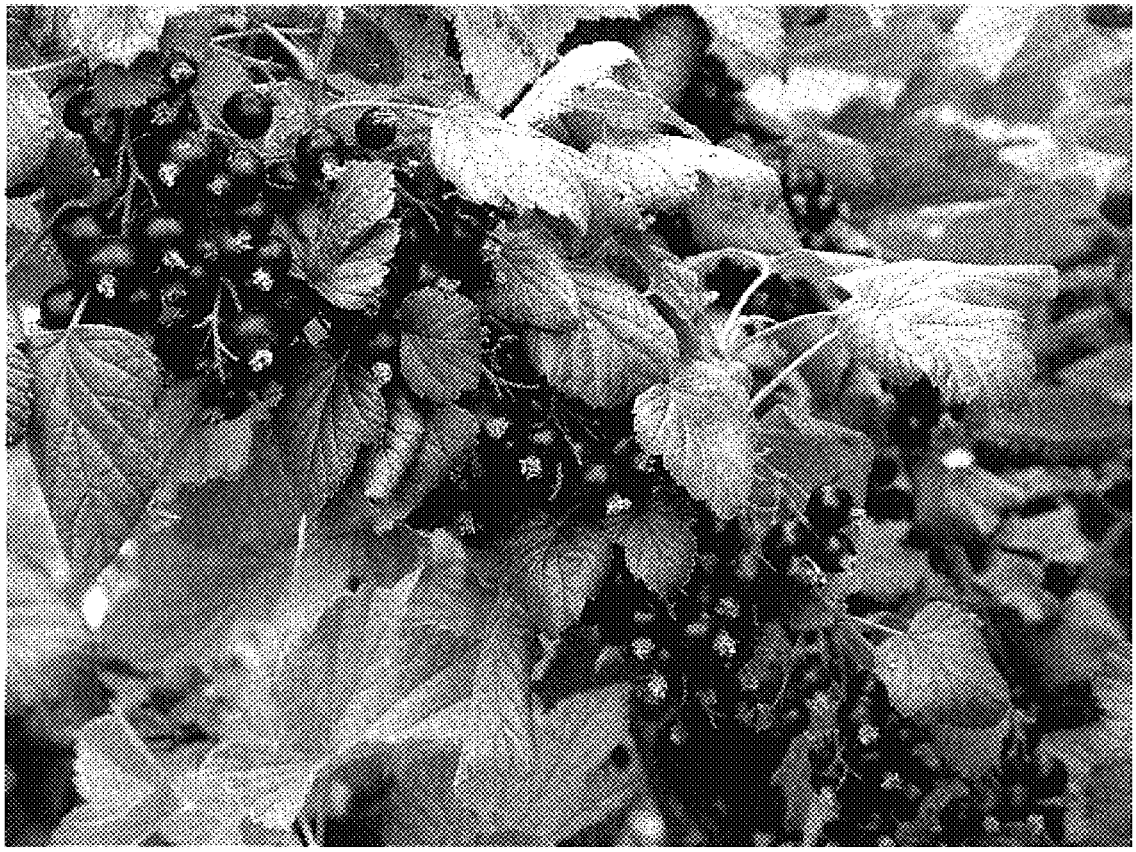
FIG. 3: Typical fruit of blackcurrant variety 'Blackadder'.
Figure 4:
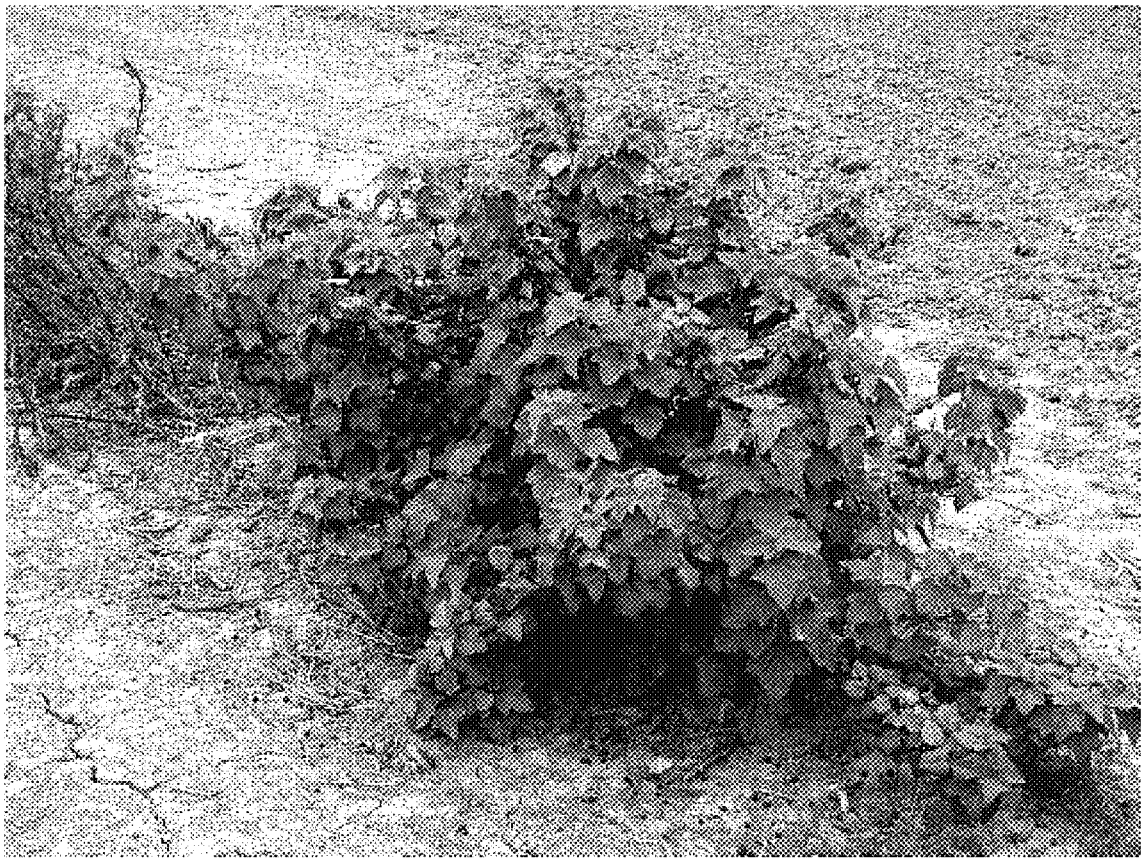
FIG. 4: Typical plant of blackcurrant variety 'Blackadder'.
Figure 5:
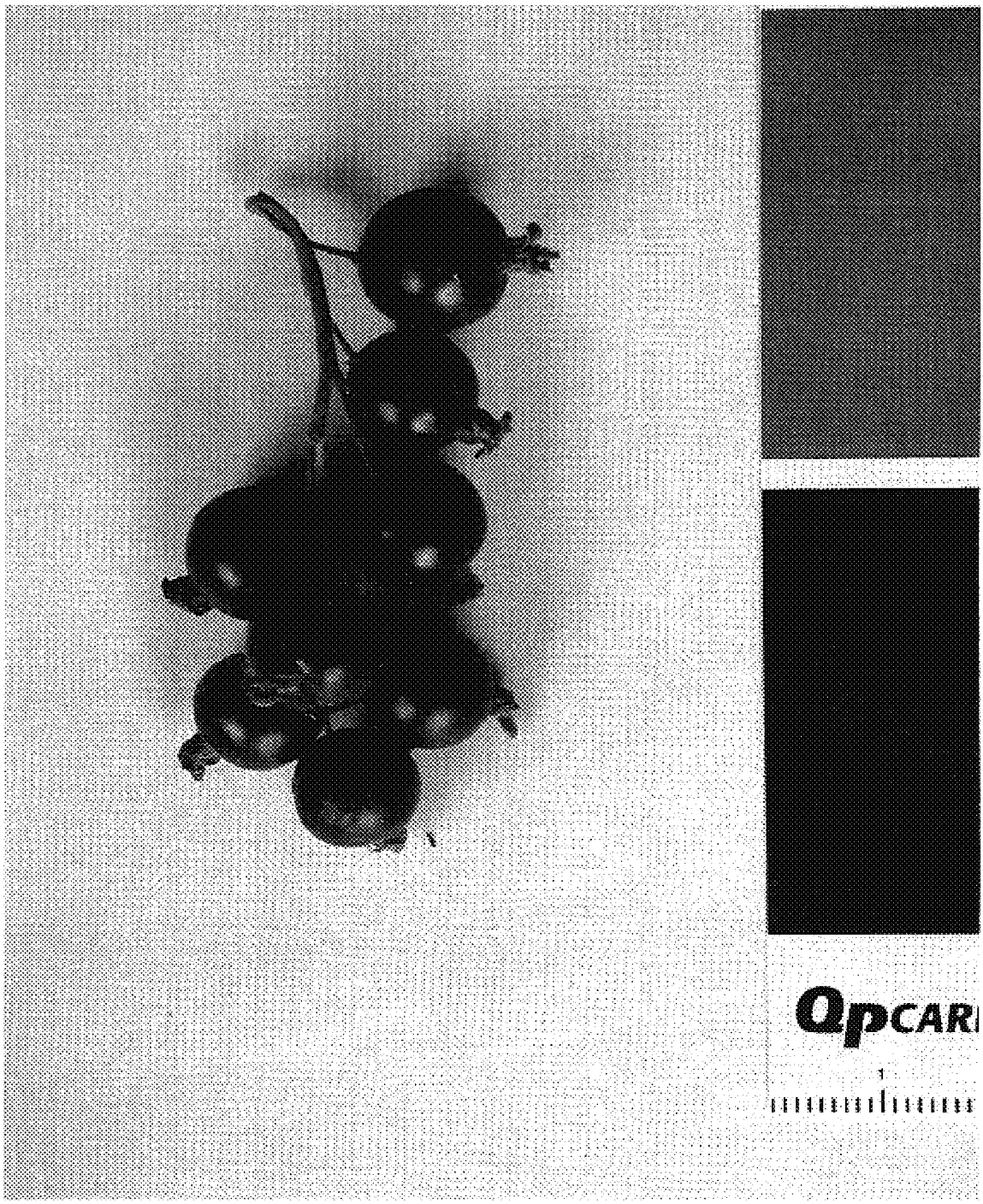
FIG. 5: Close up view of typical fruit of blackcurrant variety 'Blackadder'.
Figure 6:
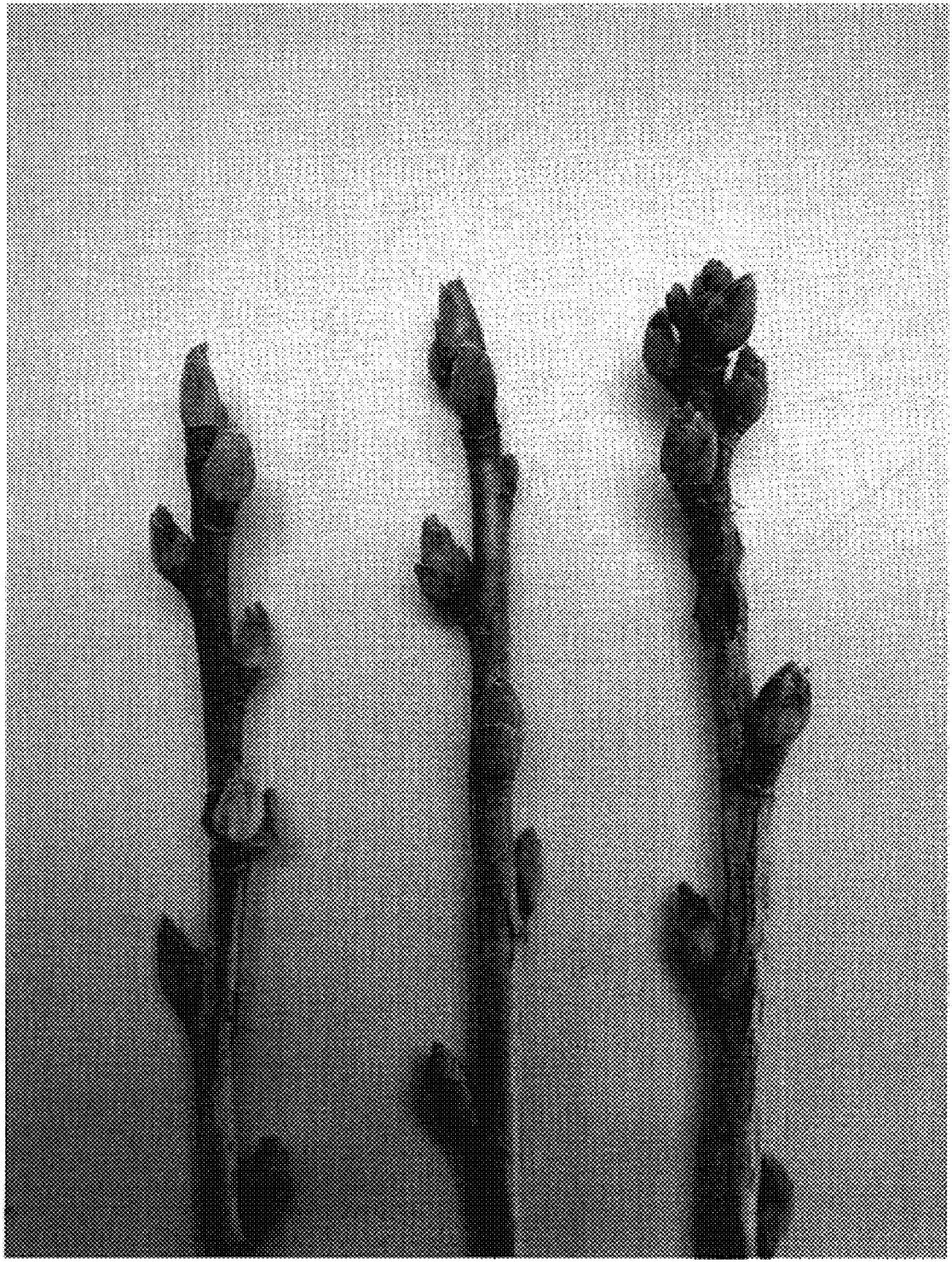
FIG. 6: Vegetative buds in winter, typical of blackcurrant variety 'Blackadder'.

The following is a detailed description of the new variety. The specimens described were grown in Canterbury, New Zealand. The observations were made in the 2005/2006 season, on plants that were planted in 2001 and managed under standard farm practices.

Horticultural terminology is used in accordance with UPOV guidelines for blackcurrant. All dimensions in millimeters, weights in grams (unless otherwise stated). Colour references refer to the R.H.S. Colour Chart, The Royal Horticultural Society, London. ($4^{th}$ edition, 2001).

Plant and Foliage

The plant exhibits an upright growth habit, although over the harvest period the branches tend to branch out with a full crop. Four year old bushes commonly have a height around 1000 mm, and a width of approximately 1000 mm, although this may vary with growing conditions. The number of basal shoots in unpruned, four year old bushes is typically around 6. One year old wood in winter is an orange-brown colour (greyed orange group 167A). Dormant buds are slightly held out in relation to the shoot. The buds are medium in length around 0.9 cm, ovate in shape and the shape of the bud apex is obtuse. The buds have a medium intensity of anthocyanin colouration and bloom. Young vegetative shoots have a medium intensity of anthocyanin colouration.

The first mature leaf typically averages approximately 90 mm in length and approximately 90 mm in width. The overall leaf shape is 5 lobed with a terminal central lobe, 2 lateral and 2 basal lobes with an acute leaf apex. The leaf base is cordate in shape and moderately open. The leaf margin is serrated. The upper surface of the leaf is medium green in colour (green group 137A) with moderate gloss. The venation is reticulate, does not differ significantly in colour from the upper surface of the leaf. The lower surface has no pubescence. The leaf petiole of the first mature leaf is yellow-green in colour (near 144B) and has weak anthocyanin colour at the base and distal ends. It is typically 60 mm in length. There is no readily discernible difference between flower and vegetative buds prior to budbreak.

Inflorescence

Flowers are configured in an inflorescence and are hermaphrodite. The attitude of the inflorescence is outwards in relation to the shoot. Predominantly the number of inflorescences per bud is usually at least 2. The length of the inflorescence typically averages 50 mm and the number of flowers per inflorescence typically averages 8. The petals of the flowers are not noticeable compared with the five sepals which are much larger than the petals. The flower diameter is typically around 8 mm. The intensity of anthocyanin colouration of the sepal is weak and of the ovary, absent to very weak. The flowers have no fragrance.

Fruit

The fruit are overall medium in size, averaging 0.8 g in weight and 10 mm in diameter. The degree of variability in berry size is moderate, fruit weights typically ranging from 0.5–1 g. The fruit colour is black (black group 202A) and has medium glossiness. The fruit are round in shape. The flesh color is pale green (near greyed-green 192D).

At maturity the fruit sweetness averages approximately 16° Brix. Ascorbic acid levels are medium, ranging from 125–150 mg/100 g and the total anthocyanin content is typically around 460 mg/100 g. Yields are high averaging approximately 15 tonnes/hectare under New Zealand growing conditions.

Cultivation

Bud burst is early, late August in New Zealand. Flowering usually commences in September and is early in relation to other cultivars. The variety is self-fertile. Fruit is harvested early in the blackcurrant harvest season in New Zealand, in early January. The main use of the fruit is juice processing and the variety is suitable for machine harvest. Fruit is typically taken direct from the field to the processing facility.

Pest and Disease Resistance

No pest and disease resistance was observed. The new variety was found to be susceptible to gall mite (*Cecidophyopsis ribis*).

We claim:

1. A new and distinct blackcurrant plant named 'Blackadder' as herein illustrated and described.

* * * * *

UNITED STATES PATENT AND TRADEMARK OFFICE

CERTIFICATE OF CORRECTION

PATENT NO. : PP 18,790 P3
APPLICATION NO. : 11/510270
DATED : May 6, 2008
INVENTOR(S) : Catherine Snelling et al.

It is certified that error appears in the above-identified patent and that said Letters Patent is hereby corrected as shown below:

Title page:
Item (73), Assignee: Delete "Mr. Albert (NZ)" and replace with --Mt. Albert (NZ)--

Signed and Sealed this

Twenty-ninth Day of July, 2008

JON W. DUDAS
*Director of the United States Patent and Trademark Office*